US 9,352,075 B2

(12) United States Patent
Robinson et al.

(10) Patent No.: US 9,352,075 B2
(45) Date of Patent: May 31, 2016

(54) WOUND HEALING APPARATUS FOR PROMOTING GRANULATION AND EPITHELIALIZATION AT A TISSUE SITE

(75) Inventors: Timothy Mark Robinson, Basingstoke (GB); Christopher Brian Locke, Bournemouth (GB); Richard Daniel John Coulthard, Verwood (GB)

(73) Assignee: KCI Licensing, Inc., San Antonio, TX (US)

(*) Notice: Subject to any disclaimer, the term of this patent is extended or adjusted under 35 U.S.C. 154(b) by 831 days.

(21) Appl. No.: 13/311,873

(22) Filed: Dec. 6, 2011

(65) Prior Publication Data
US 2012/0143113 A1    Jun. 7, 2012

Related U.S. Application Data

(60) Provisional application No. 61/420,678, filed on Dec. 7, 2010.

(51) Int. Cl.
*A61F 13/00* (2006.01)
*A61B 19/00* (2006.01)
(Continued)

(52) U.S. Cl.
CPC .............. *A61M 1/0088* (2013.01); *A61F 13/00* (2013.01); *A61F 13/00008* (2013.01); (Continued)

(58) Field of Classification Search
CPC .............. A61F 13/00; A61F 13/00008; A61F 13/0021; A61F 13/00034; A61F 13/00038; A61F 13/00042; A61F 13/00046; A61F 2013/00089; A61M 1/00; A61M 1/0023; A61M 1/34; A61M 1/0088; A61L 15/00; A61L 15/16

USPC ........ 602/41–43, 47, 53, 58, 60, 75; 128/846, 128/849; 601/6, 9, 11; 600/156, 159
See application file for complete search history.

(56) References Cited

U.S. PATENT DOCUMENTS 1,355,846 A    10/1920 Rannells
2,547,758 A    4/1951 Keeling
(Continued)

FOREIGN PATENT DOCUMENTS

AU    550575 A1    8/1982
AU    745271       4/1999
(Continued)

OTHER PUBLICATIONS

International Search Report for corresponding PCT Application No. PCT/US2011/063397 mailed Jun. 14, 2012.
(Continued)

*Primary Examiner* — Alireza Nia
*Assistant Examiner* — Brandon L Jackson

(57) ABSTRACT

An apparatus for promoting granulation and epithelialization at a tissue site having a substantially gas impermeable, flexible mat. A plurality of projections extend from a surface of the substantially gas impermeable, flexible mat, and each projection has a first end connected to the surface and a second end opposing the first end. A flexible membrane is positioned adjacent the second end of at least a portion of the plurality of projections and the flexible membrane is sufficiently flexible to allow deformation of the flexible membrane by the at least the portion of the plurality of projections when a biasing force exerted on the substantially gas impermeable, flexible mat or the plurality of projections is greater than or equal to a threshold force.

20 Claims, 9 Drawing Sheets

(51) Int. Cl.

| | | |
|---|---|---|
| A61B 1/12 | (2006.01) | |
| A61H 7/00 | (2006.01) | |
| A61F 15/00 | (2006.01) | |
| A61F 13/06 | (2006.01) | |
| A61L 15/00 | (2006.01) | |
| A61M 1/00 | (2006.01) | |
| A61L 15/16 | (2006.01) | |
| A61M 1/34 | (2006.01) | |

(52) U.S. Cl.
CPC .... *A61F 13/00034* (2013.01); *A61F 13/00038* (2013.01); *A61F 13/00042* (2013.01); *A61F 13/00046* (2013.01); *A61F 13/00068* (2013.01); *A61L 15/00* (2013.01); *A61L 15/16* (2013.01); *A61M 1/00* (2013.01); *A61M 1/0023* (2013.01); *A61M 1/34* (2013.01); *A61F 2013/00536* (2013.01)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Guiles, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielson |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A * | 8/1995 | Todd et al. .................. 604/313 |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2007/0179419 A1 * | 8/2007 | Simpson .................. 602/57 |
| 2007/0185463 A1 | 8/2007 | Mulligan |
| 2010/0069858 A1 | 3/2010 | Olson |
| 2010/0160876 A1 | 6/2010 | Robinson |
| 2012/0123220 A1 * | 5/2012 | Iyer et al. .................. 600/300 |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | WO 80/02182 | 10/1980 |
| WO | WO 87/04626 | 8/1987 |
| WO | WO 90/10424 | 9/1990 |
| WO | WO 93/09727 | 5/1993 |

(56) References Cited

FOREIGN PATENT DOCUMENTS

| WO | WO 94/20041 | 9/1994 |
|---|---|---|
| WO | WO 96/05873 | 2/1996 |
| WO | WO 97/18007 | 5/1997 |
| WO | WO 99/13793 | 3/1999 |

OTHER PUBLICATIONS

N.A. Bagautdinov, "Variant of External Vacuum Aspiration in the Treatment of Purulent Diseases of the Soft Tissues," *Current Problems in Modern Clinical Surgery: Interdepartmental Collection*, edited by V. Ye Volkov et al. (Chuvashia State University, Cheboksary U.S.S.R. 1986);pp. 94-96.
Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Les Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, Managing Draining Wounds and Fistulae: "New and Established Methods," *Chronic Wound Care*, edited by D. Krasner (Health Management Publications, Inc., King of Prussia, PA 1990), pp. 240-246.
G. Živadinović, V. Đukić, Ž. Maksimović, Đ. Radak, and P. Peška, "Vacuum Therapy in the Treatment of Peripheral Blood Vessels," *Timok Medical Journal* 11 (1986), pp. 161-164.
F.E. Johnson, "An Improved Technique for Skin Graft Placement Using a Suction Drain," *Surgery, Gynecology, and Obstetrics* 159 (1984), pp. 584-585.
A.A. Safronov, Dissertation Abstract, *Vacuum Therapy of Trophic Ulcers of the Lower Leg with Simultaneous Autoplasty of the Skin* (Central Scientific Research Institute of Traumatology and Orthosedics, Moscow, U.S.S.R. 1967).
M. Schein, R. Saadia, J.R. Jamieson, and G.A.G. Decker, "The 'Sandwich Technique' in the Management of the Open Abdomen," *British Journal of Surgery* 73 (1986), pp. 369-370.
D.E. Tribble, An Improved Sump Drain-Irrigation Device of Simple Construction, *Archives of Surgery* 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).
C.E. Tennants, "The Use of Hypermia in the Postoperative Treatment of Lesions of the Extremities and Thorax," *Journal of the American Medical Association* 64 (1915), pp. 1548-1549.
Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gork , U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007).

\* cited by examiner

WOUND HEALING APPARATUS FOR PROMOTING GRANULATION AND EPITHELIALIZATION AT A TISSUE SITE

CROSS-REFERENCE TO RELATED APPLICATIONS

This application claims the benefit of U.S. Provisional Application No. 61/420,678, filed Dec. 7, 2010, which is hereby incorporated by reference.

BACKGROUND OF THE INVENTION

1. Field of the Invention

The present invention relates generally to reduced pressure treatment systems and more particularly to a wound healing apparatus for promoting granulation and epithelialisation at a tissue site.

2. Description of Related Art

Clinical studies and practice have shown that providing a reduced pressure in proximity to a tissue site augments and accelerates the growth of new tissue at the tissue site. The applications of this phenomenon are numerous, but one particular application of reduced pressure involves treating wounds. This treatment (frequently referred to in the medical community as "negative pressure wound therapy," "reduced pressure therapy," or "vacuum therapy") provides a number of benefits, including migration of epithelial and subcutaneous tissues, improved blood flow, and micro-deformation of tissue at the wound site. Together these benefits result in increased development of granulation tissue and faster healing times. Typically, reduced pressure is applied by a reduced pressure source to tissue through a porous pad or other manifold device. The porous pad contains cells or pores that are capable of distributing reduced pressure to the tissue and channeling fluids that are drawn from the tissue. The porous pad often is incorporated into a dressing having other components that facilitate treatment.

SUMMARY

The problems presented by existing reduced pressure systems and wound healing pads are solved by the systems and methods of the illustrative embodiments described herein. An apparatus for promoting granulation and epithelialisation at a tissue site includes a substantially gas impermeable, flexible mat. A plurality of projections extend from a surface of the substantially gas impermeable, flexible mat, and each projection has a first end connected to the surface and a second end opposing the first end. A flexible membrane is positioned adjacent the second end of at least a portion of the plurality of projections and the flexible membrane is sufficiently flexible to allow deformation of the flexible membrane by the at least a portion of the plurality of projections when a biasing force exerted on the substantially gas impermeable, flexible mat or the plurality of projections is greater than or equal to a threshold force.

In another embodiment, an apparatus for promoting granulation and epithelialisation at a tissue site includes a hollow mat having an inner chamber and a plurality of recesses disposed in proximity to a first surface of the hollow mat. An extendable projection is positioned within each recess and configured to extend from the recess when a pressure ($p_1$) within the inner chamber is greater than a pressure ($p_2$) in the recess.

In still another embodiment, an apparatus for promoting granulation and epithelialisation at a wound includes a porous pad having a first compressibility. A plurality of granulation promoters are embedded within the porous pad and have a second compressibility less than the first compressibility of the porous pad. The granulation promoters are positioned near a surface of the porous pad. A biasing force applied to the porous pad or granulation promoters that is greater than or equal to a threshold amount causes the granulation promoters to extend from the porous pad or alters the surface of the porous pad to promote granulation.

In yet still another embodiment, an apparatus for promoting granulation and epithelialisation of a tissue site includes a porous, reticulated foam having a tissue-contacting surface that is sufficiently rough to promote granulation. A hydrogel-forming material is disposed in at least a portion of the porous, reticulated foam such that the introduction of a liquid into the porous pad causes the hydrogel-forming material to moisten and expand, thereby altering the tissue-contacting surface to be sufficiently smooth to promote epithelialisation.

In another embodiment, a reduced pressure treatment system for administering reduced pressure treatment to a tissue site includes a reduced pressure source and a manifold in fluid communication with the reduced pressure source to provide a reduced pressure to the tissue site. The manifold has a tissue-contacting surface in contact with the tissue site, and the tissue-contacting surface has a granulation configuration and an epithelialisation configuration such that at least one of the granulation configurations and the epithelialisation configurations is activated by an activation stimulus.

In still another embodiment, a reduced pressure treatment system for administering reduced pressure treatment to a tissue site includes a reduced pressure source and an apparatus fluidly coupled to the reduced pressure source and positioned at the tissue site. The apparatus includes a substantially gas impermeable, flexible mat. A plurality of projections extend from a surface of the substantially gas impermeable, flexible mat, and each projection has a first end connected to the surface and a second end opposing the first end. A flexible membrane is positioned adjacent the second end of at least a portion of the plurality of projections and the flexible membrane is sufficiently flexible to allow deformation of the flexible membrane by the at least a portion of the plurality of projections when a biasing force exerted on the substantially gas impermeable, flexible mat or the plurality of projections is greater than or equal to a threshold force. A drape formed of substantially impermeable material covers the apparatus and the tissue site to substantially maintain the reduced pressure at the tissue site.

In another embodiment, a reduced pressure treatment system for administering reduced pressure treatment to a tissue site includes a reduced pressure source and an apparatus fluidly coupled to the reduced pressure source and positioned at the tissue site. The apparatus includes a hollow mat having an inner chamber and a plurality of recesses disposed in proximity to a first surface of the hollow mat. An extendable projection is positioned within each recess and configured to extend from the recess when a pressure ($p_1$) within the inner chamber is greater than a pressure ($p_2$) in the recess. A drape formed of substantially impermeable material covers the apparatus and the tissue site to substantially maintain the reduced pressure at the tissue site.

In yet still another embodiment, a reduced pressure treatment system for administering reduced pressure treatment to a tissue site includes a reduced pressure source and an apparatus fluidly coupled to the reduced pressure source and positioned at the tissue site. The apparatus includes a porous pad having a first compressibility. A plurality of granulation promoters are embedded within the porous pad and have a second compressibility less than the first compressibility of the porous pad. The granulation promoters are positioned near a surface of the porous pad. A biasing force applied to the porous pad or granulation promoters that is greater than or equal to a threshold amount causes the granulation promoters to extend from the porous pad or alters the surface of the porous pad to promote granulation. A drape formed of substantially impermeable material covers the apparatus and the tissue site to substantially maintain the reduced pressure at the tissue site.

In another embodiment, a reduced pressure treatment system for administering reduced pressure treatment to a tissue site includes a reduced pressure source and an apparatus fluidly coupled to the reduced pressure source and positioned at the tissue site. The apparatus includes a porous, reticulated foam having a tissue-contacting surface that is sufficiently rough to promote granulation. A hydrogel-forming material is disposed in at least a portion of the porous, reticulated foam such that the introduction of a liquid into the porous pad causes the hydrogel-forming material to moisten and expand, thereby altering the tissue-contacting surface to be sufficiently smooth to promote epithelialisation. A drape formed of substantially impermeable material covers the apparatus and the tissue site to substantially maintain the reduced pressure at the tissue site.

In still another embodiment, a reduced pressure treatment system having a reduced pressure source and a manifold may be paired with any of the apparatuses described herein.

In another embodiment, a method for selectively promoting granulation and epithelialisation of a tissue site includes positioning a pad having a tissue-contacting surface at the tissue site. Reduced pressure is applied to the tissue site when the tissue-contacting surface is in a first configuration to promote granulation. The first configuration of the tissue-contacting surface is changed to a second configuration. A reduced pressure is applied to the tissue site when the tissue-contacting surface is in the second configuration to promote epithelialisation.

Other objects, features, and advantages of the illustrative embodiments will become apparent with reference to the drawings and detailed description that follow.

DETAILED DESCRIPTION OF ILLUSTRATIVE EMBODIMENTS

In the following detailed description of several illustrative embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims. Unless otherwise indicated, as used herein, "or" does not require mutual exclusivity.

The term "reduced pressure" as used herein generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure associated with tissue at the tissue site. Although the terms "vacuum" and "negative pressure" may be used to describe the pressure applied to the tissue site, the actual pressure reduction applied to the tissue site may be significantly less than the pressure reduction normally associated with a complete vacuum. Reduced pressure may initially generate fluid flow in the area of the tissue site. As the hydrostatic pressure around the tissue site approaches the desired reduced pressure, the flow may subside, and the reduced pressure is then maintained. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

Figure 1:
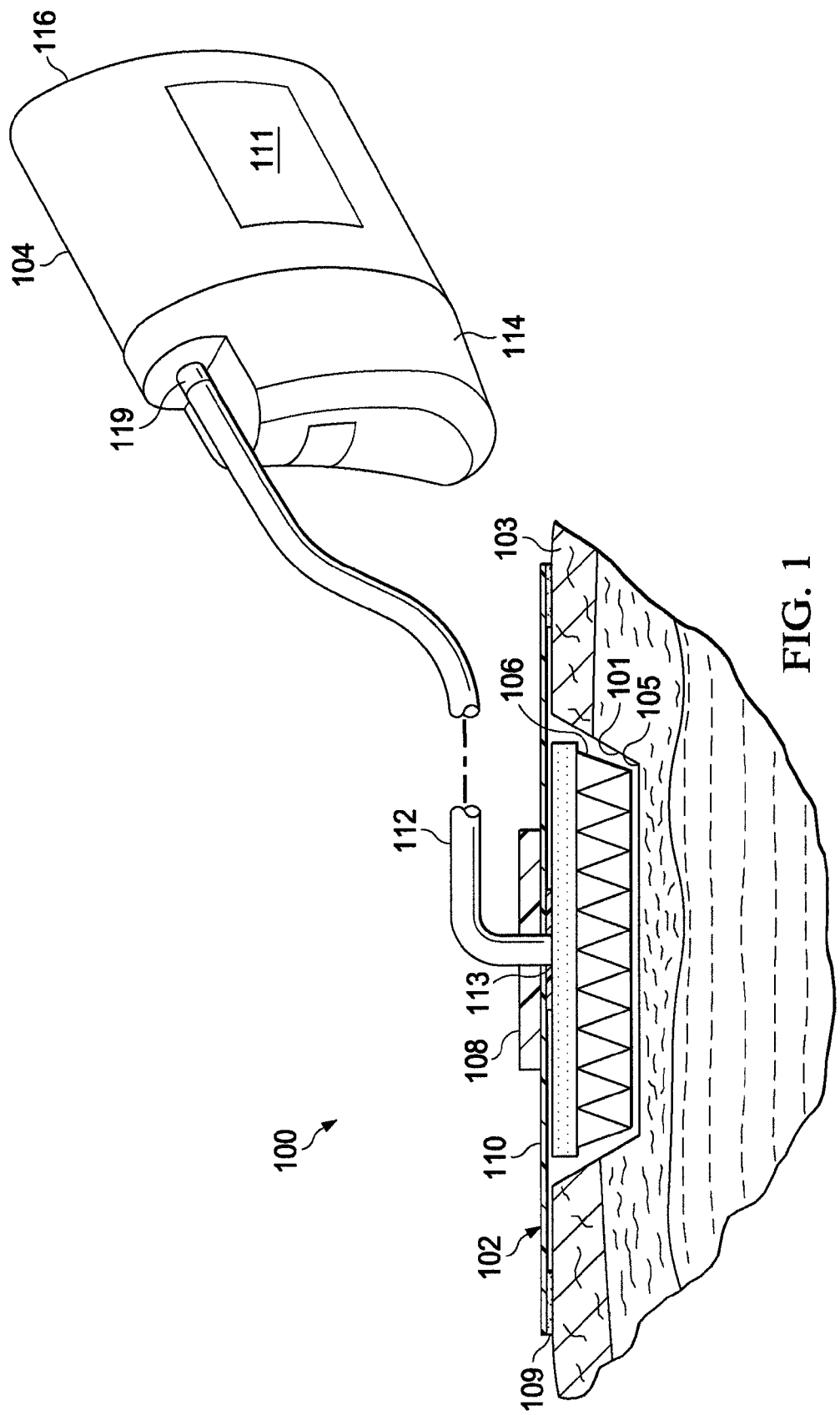
FIG. 1 illustrates a perspective view with a portion shown in cross-section of a reduced pressure treatment system for administering reduced pressure treatment to a tissue site according to an illustrative embodiment.

Referring to FIG. 1, an illustrative embodiment of a reduced pressure treatment system 100 for treating a tissue site 101 on a patient with reduced pressure includes a dressing 102 placed proximate to the tissue site 101 and a reduced pressure treatment device 104 fluidly coupled to the dressing 102. The dressing 102 includes a wound healing apparatus 106 for promoting both granulation and epithelialisation of the tissue site 101. As used herein, the term "tissue site" may refer to a wound, such as a wound 105, or defect located on or within any tissue, including but not limited to, bone tissue, adipose tissue, muscle tissue, neural tissue, dermal tissue, vascular tissue, connective tissue, cartilage, tendons, or ligaments. The term "tissue site" may further refer to areas of any tissue that are not necessarily wounded or defective, but are instead areas in which it is desired to add or promote the growth of additional tissue. For example, reduced pressure tissue treatment may be used in certain tissue areas to grow additional tissue that may be harvested and transplanted to another tissue location.

The wound healing apparatus 106 may be a manifold or fluidly connected to a manifold. The term "manifold" as used herein generally refers to a substance or structure that is provided to assist in applying reduced pressure to, delivering fluids to, or removing fluids from the tissue site 101. The manifold typically includes a plurality of flow channels or pathways that distribute fluids provided to and removed from the tissue site around the manifold. In one illustrative embodiment, the flow channels or pathways are interconnected to improve distribution of fluids provided or removed from the tissue site 101. Examples of manifolds may include, for example, without limitation, devices that have structural elements arranged to form flow channels, such as, for example, cellular foam, open-cell foam, porous tissue collections, liquids, gels, and foams that include, or cure to include, flow channels. In one embodiment, the wound healing apparatus 106 includes a porous foam and having a plurality of interconnected cells or pores that act as flow channels. The porous foam may be a polyurethane, open-cell, reticulated foam such as GranuFoam® material manufactured by Kinetic Concepts, Incorporated of San Antonio, Tex. Other embodiments may include "closed cells."

The dressing 102 further includes a reduced pressure interface 108 fluidly coupled to the wound healing apparatus 106 and a drape 110. In one embodiment, a manifold (not shown) is positioned between the reduced pressure interface 108 and the wound healing apparatus 106 for distributing pressure or facilitating fluid communication between the reduced pressure interface 108 and the wound healing apparatus 106. The drape 110, or cover, may be placed over the wound healing apparatus 106 and a portion of a patient's epidermis 103 to create a fluid seal between the drape 110 and the epidermis 103. The drape 110 may include an adhesive 109 or bonding agent to secure the drape 110 to the epidermis 103. In one embodiment, the adhesive 109 may be used to create a seal between the drape 110 and the epidermis 103 to prevent leakage of reduced pressure from the tissue site 101. In another embodiment, a seal layer (not shown) such as, for example, a hydrogel or other material may be disposed between the drape 110 and the epidermis 103 to augment or substitute for the sealing properties of the adhesive 109. As used herein, "fluid seal" means a seal adequate to maintain reduced pressure at a desired site given the particular reduced pressure source involved.

The reduced pressure interface 108 may be positioned adjacent to or coupled to the drape 110 to provide fluid access to the wound healing apparatus 106. The drape 110 has an aperture 113 for providing fluid access to the reduced pressure interface 108. In one embodiment, the drape 110 is placed over the reduced pressure interface 108 and a portion of the patient's epidermis 103 to create a fluid seal between the drape 110 and the epidermis 103. A reduced pressure delivery conduit 112 fluidly couples the reduced pressure treatment device 104 and the reduced pressure interface 108. The reduced pressure interface 108 allows the reduced pressure to be delivered to the tissue site 101. While the amount and nature of reduced pressure applied to the tissue site 101 will typically vary according to the application, in one embodiment, the reduced pressure treatment device 104 may provide reduced pressures between about 0 mm Hg and about −500 mm Hg and more specifically between about −125 mm Hg and about −300 mm Hg for promoting granulation, and between about 0 mm Hg and about −125 mm Hg for promoting epithelialisation.

The reduced pressure treatment device 104 may include a collection canister 114 in fluid communication with a reduced pressure source 116. The reduced pressure delivery conduit 112 may be a multi-lumen tube that provides a continuous conduit between the reduced pressure interface 108 and an inlet 119 positioned on the collection canister 114. Liquids or exudates communicated from the wound healing apparatus 106 through the reduced pressure delivery conduit 112 are removed from the reduced pressure delivery conduit 112 and retained within the collection canister 114.

In the embodiment illustrated in FIG. 1, the reduced pressure source 116 is an electrically-driven vacuum pump. In another implementation, the reduced pressure source 116 may instead be a manually-actuated or manually-charged pump that does not require electrical power. The reduced pressure source 116 instead may be any other type of reduced pressure pump, or alternatively a wall suction port such as those available in hospitals and other medical facilities. The reduced pressure source 116 may be housed within or used in conjunction with the reduced pressure treatment device 104, which may also contain sensors, processing units, alarm indicators, memory, databases, software, display units, and user interfaces 111 that further facilitate the application of reduced pressure treatment to the tissue site 101. In one example, pressure-detection sensors (not shown) may be disposed at or near the reduced pressure source 116. The pressure-detection sensors may receive pressure data from the reduced pressure interface 108 via lumens in the reduced pressure delivery conduit 112 that are dedicated to delivering reduced pressure data to the pressure-detection sensors. The pressure-detection sensors may communicate with a processing unit that monitors and controls the reduced pressure that is delivered by the reduced pressure source 116.

Figure 2A:
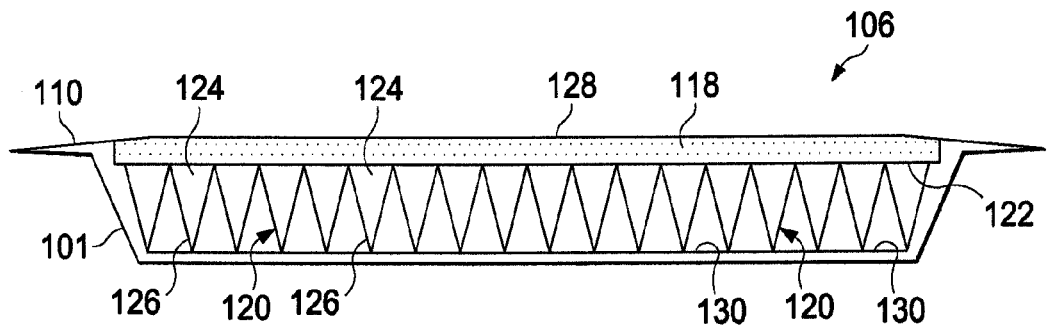
FIG. 2A illustrates a cross-sectional view of an illustrative, non-limiting embodiment of a wound healing apparatus of the reduced pressure treatment system of FIG. 1 in a state for promoting epithelialisation.
Figure 2B:
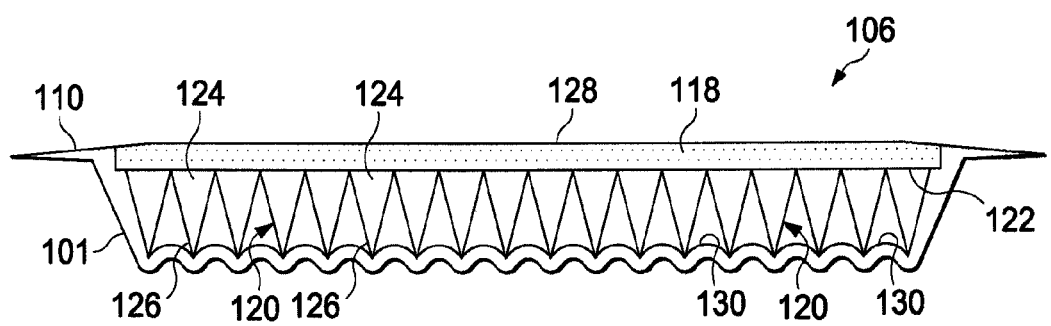
FIG. 2B illustrates a cross-sectional view of the wound healing apparatus of FIG. 2A in a state for promoting granulation.

Referring now to FIGS. 2A and 2B, an illustrative embodiment of the wound healing apparatus 106 positioned proximate the tissue site 101 and covered with the drape 110 is presented in more detail. The wound healing apparatus 106 includes a plurality of projections 120 extending from a mat 118. In one embodiment, the mat 118 may be substantially gas impermeable and flexible. The wound healing apparatus 106 has a first configuration for promoting epithelialisation as shown in FIG. 2A and a second configuration for promoting granulation as shown in FIG. 2B. In the first configuration shown in FIG. 2A, a flexible membrane 130 covers the projections 120 and presents a substantially smooth surface to the tissue site 101. When the tissue site 101 is exposed to a substantially smooth surface in the presence of reduced pressure, epithelialisation is encouraged. When reduced pressure and a more rough surface such as that shown in FIG. 2B is presented to the tissue site 101, granulation is encouraged. As illustrated in FIG. 2B, the projections 120 are capable of deforming the flexible membrane 130 to present a rougher surface to the tissue site 101. The rough surface presented by the projections 120 causes microstrains and microstresses to be applied to the tissue site 101, which increases granulation.

The substantially gas impermeable, flexible mat 118 includes a plurality of channels 128 for allowing the passage of fluids through the mat 118 to or from the tissue site 101. The substantially gas impermeable, flexible mat 118 may, for example, be a polyurethane (PU), thermoplastic elastomer (TPE), or silicone elastomer material. The plurality of projections 120 extend from a surface 122 of the substantially gas impermeable, flexible mat 118 and may be in fluid communication with the substantially gas impermeable, flexible mat 118. Each projection 120 has a first end 124 connected to the surface 122 of the substantially gas impermeable, flexible mat 118 and a second end 126 opposing the first end 124. The first end 124 of each projection 120 may be bonded or similarly fixed to the surface 122. The plurality of projections 120 may be any shape or size; for example the plurality of projections 120 may be spikes, rods, pins, tubes, or other protrusions, etc. The plurality of projections 120 may be made from a range of polymers such as a polyurethane (PU), thermoplastic elastomer (TPE), or silicone elastomer material and may have a range of compressibility or hardness such as $10°$-$100°$ Shore A. Structurally, the plurality of projections 120 may be solid, perforated, hollow, etc., or any combination thereof. The configuration of the plurality of projections 120 (the shape and structure) may enable the transmission of pressure and fluid through the plurality of projections 120 as well as modify the compressibility of the plurality of projections 120 depending on the material used.

The second end 126 of at least a portion of the plurality of projections 120 may be covered by the flexible membrane 130. In one embodiment, the flexible membrane 130 may be bonded to at least a portion of the plurality of projections 120 or similarly fixed. The flexible membrane 130 is sufficiently flexible to be deformed by at least a portion of the plurality of projections 120 and may be an elastomeric material. "Elastomeric" means having the properties of an elastomer, and generally refers to a polymeric material that has rubber-like properties. More specifically, most elastomers have elongation rates greater than 100% and a significant amount of resilience. The resilience of a material refers to the material's ability to recover from an elastic deformation. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane, EVA film, co-polyester, thermoplastic elastomers, synthetic latexes, and silicones. The flexible membrane 130 may be hydrophilic or hydrophobic.

The flexible membrane 130 may be deformed by the plurality of projections 120 when a biasing force, or other activation stimulus, is exerted on the substantially gas impermeable, flexible mat 118 and the biasing force is greater than or equal to a threshold force. In one embodiment, the flexible membrane 130 may be deformed by the plurality of projections 120 when the biasing force exerted on the plurality of projections 120 is greater than or equal to the threshold force. The deformation of the flexible membrane 130 may be in response to a combination of the biasing force exerted on the mat 118 or projections 120 and the force exerted by the tissue site on portions of the flexible membrane 130 between the projections 120. While the deformation of the flexible membrane 130 may occur as described above when the biasing force equals or exceeds a threshold force, the deformation may occur more gradually over a range of forces.

The biasing force may be in the form of reduced pressure supplied from the reduced pressure source 116. As the reduced pressure beneath the drape 110 increases (i.e. the gauge pressure decreases), the drape 110 is pulled toward the tissue site, which exerts a biasing force on the flexible mat 118 by the drape 110. In a specific, non-limiting embodiment, the amount of reduced pressure required for the biasing force to equal the threshold force may be about −125 mmHg. In other embodiments, the biasing force may be applied to the flexible mat 118 by a weight or any other force that is not generated by a reduction in pressure beneath the drape 110 but that promotes either rough or smooth surfaces to encourage granulation or epithelialisation.

Microperforations (not shown) or valves that expand or open under the influence of the biasing force may be present on the flexible membrane 130. In one embodiment, the microperforations are small apertures that extend through the flexible membrane 130. The size of the microperforations is such that when the flexible membrane 130 is not expanded, the microperforations are essentially closed thereby not allowing the transmission of pressure and fluids through the flexible membrane 130. As the flexible membrane 130 expands under the influence of the biasing force, the deformation of the flexible membrane 130 by the plurality of projections 120 expands the microperforations, which allows for the transmission of pressure and fluids. Small valves may be either operably associated with the microperforations or otherwise associated with the flexible membrane 130 to further control the passage of pressure and fluids through the flexible membrane 130. In one embodiment, the microperforations may be positioned directly beneath each of the projections 120. In another embodiment, the microperforations may be positioned in the flexible membrane 130 between projections 120. A sufficiently smooth surface for encouraging epithelialization is presented when the microperforations are closed or the flexible membrane 130 is in an unexpanded state. In one embodiment, using the Verein Deutscher Ingenieure (VDI) (3400) standard scale, a sufficiently smooth surface for promoting epithelialisation may have a surface finish of VDI (3400)<30. In a specific, non-limiting embodiment, the microperforations may be closed when the biasing force is at reduced pressure levels less than about −50 mmHg (i.e. at gauge pressures greater than about −50 mmHg). Pressures in a range between about −50 mmHg and about −125 mmHg may be sufficient to cause the microperforations to open and expand without causing the flexible membrane 130 to deform. When the flexible membrane 130 is deformed by the plurality of projections 120, the microperforations may also expand to allow for the transmission of pressure and fluids. The deformation of the flexible membrane 130 presents a rough, porous surface to the tissue site 101 for encouraging granulation. In one embodiment, a rough, porous surface may have a surface finish of VDI (3400)>30.

In operation, a health care provider may place the wound healing apparatus 106 proximate the tissue site 101 and cover the wound healing apparatus 106 with the drape 110 to create a fluid seal beneath the drape. In one embodiment, a manifold may be placed between the drape 110 and the wound healing apparatus 106. The wound healing apparatus 106 is then fluidly connected to the reduced pressure treatment device 104. Reduced pressure is supplied to the tissue site 101 via the wound healing apparatus 106. The health care provider may adjust the levels of reduced pressure supplied depending on the type of treatment sought. In one embodiment, to promote granulation the health care provider may increase the reduced pressure to levels equal to or greater than about −125 mmHg thereby causing the flexible membrane 130 to deform and present a rough, porous surface to the tissue site 101. In the presence of this reduced pressure, the rough surface presented by the projections 120 of the wound healing apparatus 106 exert a force on the tissue site 101. This force creates microstrains and microstresses at the tissue site 101, which promotes development of new granulation tissue. To promote epithelialisation, the heath care provider may decrease the reduced pressure to levels less than about −125 mmHg. These reduced pressure levels allow the projections to essentially retract such that the projections 120 no longer deform the flexible membrane 130. The flexible membrane 130 is therefore capable of presenting a smooth surface to the tissue site 101 which is more conducive to promoting epithelialisation. In one embodiment, at reduced pressure levels between about −50 mm Hg and about −125 mm Hg, the flexible membrane 130 is relatively smooth, and yet the microperforations or valves associated with the flexible membrane 130 are open, thereby allowing improved fluid removal. At reduced pressure levels less than about −50 mm Hg, the flexible membrane 130 remains smooth, and the microperforations or valves are substantially closed. Again, the smooth surface encourages epithelialisation, and the reduced pressure aids in fluid removal, although not as much fluid as if the mircoperforations or valves were open. While specific pressure values have been presented as an example, it should be recognized that the wound healing apparatus 106 could be configured to allow deformation of the flexible membrane 130 at higher or lower pressures, thereby altering the reduced pressures required to promote either granulation or epithelialisation.

Figure 3:
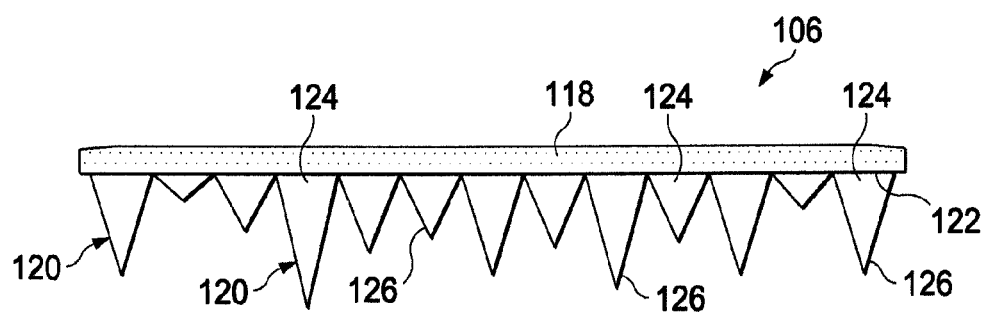
FIG. 3 illustrates a cross-sectional view of another illustrative, non-limiting embodiment of a wound healing apparatus.

Referring now primarily to FIG. 3, but also to FIGS. 1, 2A, and 2B, another illustrative embodiment of the wound healing apparatus 106 of FIGS. 1, 2A, and 2B is presented. In this embodiment, the wound healing apparatus 106 includes the substantially gas impermeable, flexible mat 118 and the plurality of projections 120 but not the flexible membrane 130. The plurality of projections 120 may be constructed from bioabsorbable materials that do not have to be removed from a patient's body following use of the wound healing apparatus 106. Suitable bioabsorbable materials may include, without limitation, a polymeric blend of polylactic acid (PLA) and polyglycolic acid (PGA). The polymeric blend may also include without limitation polycarbonates, polyfumarates, and capralactones. Additionally, each of the plurality of projections 120 may vary in shape, size, and structure relative to each other.

The presence of fluid may cause the plurality of projections 120 to dissolve. The fluid may be exudate or other fluids from the tissue site 101, or the fluid may be instilled into the tissue site 101 by a health care provider or a device associated with the reduced pressure treatment device 104 to accelerate dissolution of the plurality of projections 120. The fluid may be instilled into the tissue site 101 via the substantially gas impermeable, flexible mat 118 or the plurality of projections 120. In one embodiment, hollow or perforated projections (not shown) may communicate fluid into the tissue site 101. The plurality of projections 120 may include treatment agents such as growth factors, anti-bacterials, debriding agents, pro or anti-clogging agents, pain reducing agents, etc. that are released into the tissue site 101 as the plurality of projections 120 dissolve.

In operation, the wound healing apparatus 106 having the plurality of bioabsorbable projections 120 may be placed proximate the tissue site 101, covered with the drape 110, and fluidly connected to the reduced pressure source 116 (FIG. 1) so as to receive reduced pressure. The placement of the plurality of projections 120 into the tissue site 101 presents a sufficiently rough surface to promote granulation. When the plurality of projections 120 dissolve in the presence of fluid, the substantially gas impermeable, flexible mat 118 presents a sufficiently smooth surface to the tissue site 101 to promote epithelialisation. As previously stated, differing levels of reduced pressure may be used depending on the type of treatment desired.

Figure 4A:
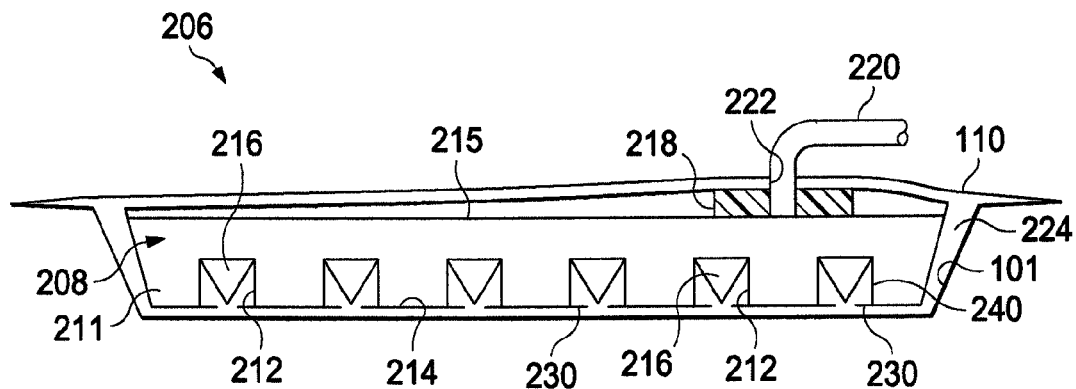
FIG. 4A illustrates a cross-sectional view of another illustrative, non-limiting embodiment of a wound healing apparatus in a state for promoting epithelialisation.
Figure 4B:
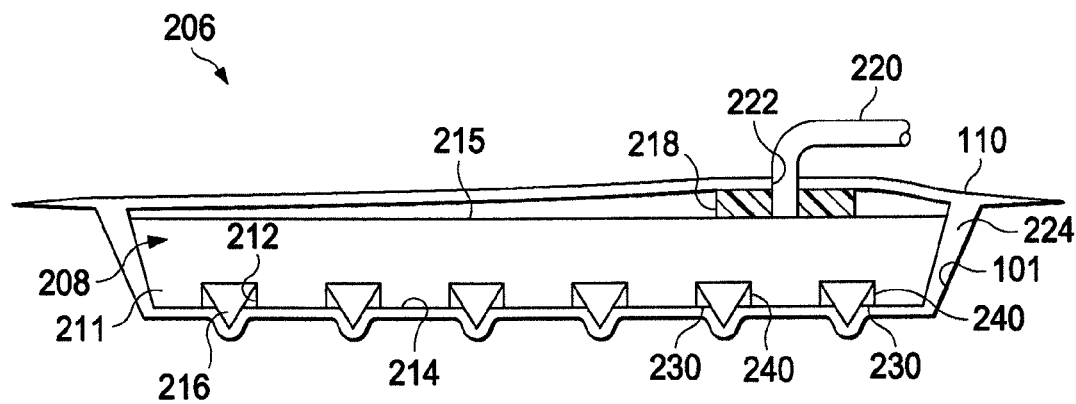
FIG. 4B illustrates a cross-sectional view of the wound healing apparatus of FIG. 4A in a state for promoting granulation.

Referring now to FIGS. 4A and 4B, another illustrative embodiment of a wound healing apparatus 206 for use in a reduced pressure treatment system (e.g., the reduced pressure treatment system 100 of FIG. 1) is presented. As shown, the wound healing apparatus 206 is positioned proximate the tissue site 101 and covered with the drape 110. The wound healing apparatus 206 includes a hollow mat 208 having an inner chamber 211 and a plurality of recesses 212 disposed in proximity to a first surface 214 of the hollow mat 208. An extendable projection 216 is positioned within each of the plurality of recesses 212 and is configured to extend from the recesses 212 when a pressure ($p_1$) within the inner chamber 211 is greater than a pressure ($p_2$) outside of the inner chamber 211 (e.g. in the recesses 212). The wound healing apparatus 206 has a first configuration for promoting epithelialisation as shown in FIG. 4A in which a relatively smooth surface is presented to the tissue site 101. In a second configuration shown in FIG. 4B, the wound healing apparatus 206 has a second configuration for promoting granulation in which a relatively rough surface is presented to the tissue site 101. As previously described, the relatively rough surface presented by the extension of projections 216 induces microstrains and microstresses at the tissue site 101 which are conducive to new granulation tissue growth.

The hollow mat 208 may be formed from a polymeric material and may be pre-sealed so that the fluid volume within the inner chamber 211 remains static during treatment. The hollow mat 208 may be formed with a plurality of sealed channels (not shown) disposed therethrough that extend from a second surface 215 to the first surface 214 to facilitate the transmission of fluid and pressure. The hollow mat 208 includes the plurality of recesses 212 for housing the extendable projections 216. The extendable projections 216 remain sheathed within the recesses 212 when the pressure ($p_2$) in the recesses 212 is greater than the pressure ($p_1$) within the inner chamber 211. When the extendable projections 216 are sheathed as shown in FIG. 4A, the wound healing apparatus 206 presents a sufficiently smooth surface to the tissue site 101 to promote epithelialisation. In one embodiment, a sufficiently smooth surface may have a surface finish of VDI (3400)<30. In the event the pressure ($p_1$) within the inner chamber 211 becomes greater than the pressure ($p_2$) in the recesses 212, the recesses 212 have one or more side walls 240 configured to collapse or compress, thereby allowing the extendable projections 216 to extend from the plurality of recesses 212 and contact the tissue site 101. When the extendable projections 216 extend into the tissue site 101, a sufficiently rough and uneven surface is presented to the tissue site for promoting granulation. In one embodiment, a sufficiently rough and uneven surface may have a surface finish of VDI (3400)>30. It should be understood that the extendable projections 216 may be any shape or size; for example the extendable projections 216 may be spikes, rods, pins, tubes, or other protrusions, etc. Additionally, the extendable projections 216 may be made from a range of low density polymers such as a thermoplastic elastomer (TPE) and may have a range of compressibility or hardness such as $10°$-$100°$ Shore A. Low density polymers may be used so that the weight of the extendable projections 216 does not force the extendable projections 216 from the recesses 212 (i.e., due to gravity).

The wound healing apparatus 206 may further include a pressurization unit 218 for changing the pressure ($p_1$) within the inner chamber 211. In one embodiment, the pressure ($p_1$) within the inner chamber 211 may be changed using the pressurization unit 218 through pneumatic or hydraulic means. The pressurization unit 218 is fluidly connected to the hollow mat 208 and may be placed adjacent the second surface 215. The pressurization unit 218 may be sealed beneath the drape 110 with a connecting tube 220 extending through an aperture 222 in the drape 110. In one embodiment (not shown), the pressurization unit 218 may be placed outside the drape 110 and fluidly connected to the hollow mat 208 through an aperture in the drape 110. In another embodiment, atmospheric air could be supplied to the inner chamber 211 when the reduced pressure is applied to the wound healing apparatus 206 thereby allowing the pressure ($p_1$) within the inner chamber 211 to be greater than the pressure ($p_2$) in the recesses 212. Alternatively, if the inner chamber 211 is sealed as previously described, and the pressure of air within the inner chamber 211 is at approximately atmospheric pressure, the application of reduced pressure beneath the drape 110 will result in an extension of the projections 216.

In operation, a health care provider may place the wound healing apparatus 206 proximate the tissue site 101 and cover the wound healing apparatus 206 with the drape 110 to create a sealed space 224 beneath the drape. In one embodiment, a manifold may be placed between the drape 110 and the wound healing apparatus 206. The sealed space 224 is then fluidly connected to a reduced pressure treatment device. Reduced pressure is supplied to the tissue site 101 at desired treatment levels. In one embodiment, the wound healing apparatus 206, or the hollow mat 208, is pre-sealed so that the level of reduced pressure supplied to the sealed space 224 determines whether the wound healing apparatus 206 is configured to promote granulation or epithelialisation, i.e., whether the pressure ($p_2$) in the recesses 212 is less than or greater than the pressure ($p_1$) within the inner chamber 211 of the hollow mat 208. In another embodiment, the pressure ($p_1$) within the inner chamber 211 may be changed by the pressurization unit 218. In this instance, both the pressurization unit 218 and the level of reduced pressure supplied to the sealed space determines whether the wound healing apparatus 206 is configured to promote either granulation or epithelialisation, or combinations thereof. In some embodiments, it may be desired to configure the wound healing apparatus 206 such that granulation is promoted in one area of the tissue site while epithelialisation simultaneously is promoted at another area of the tissue site. This may be accomplished by only presenting projections or a rough surface to the tissue site in areas where granulation is desired. In those areas where epithelialisation is desired, a smoother surface would be presented to the tissue site.

Figure 4C:
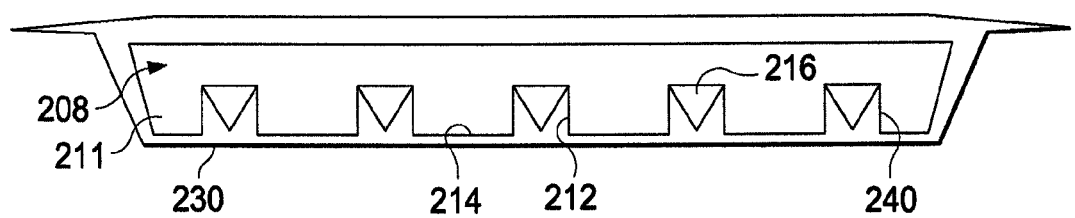
FIG. 4C illustrates a cross-sectional view of another illustrative, non-limiting embodiment of the wound healing apparatus of FIG. 4A.
Figure 4D:
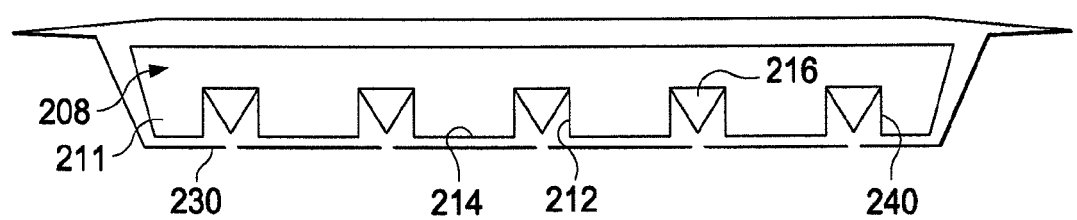
FIG. 4D illustrates a cross-sectional view of another illustrative, non-limiting embodiment of the wound healing apparatus of FIG. 4A.
Figure 4E:
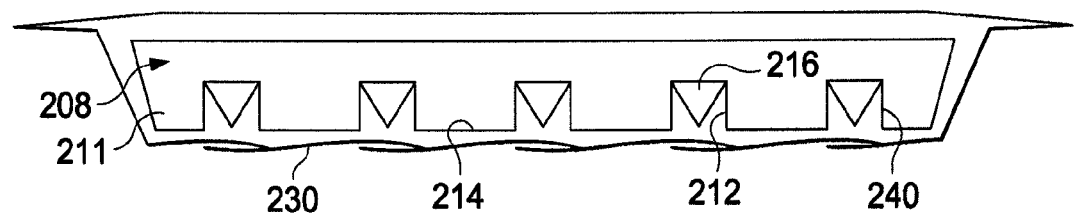
FIG. 4E illustrates a cross-sectional view of another illustrative, non-limiting embodiment of the wound healing apparatus of FIG. 4A.

Referring now primarily to FIGS. 4C-4E, but still with reference to FIGS. 4A and 4B, the wound healing apparatus 206 is further shown in alternative embodiments that include a flexible membrane 230 placed over the plurality of recesses 212 covering the extendable projections 216. The flexible membrane 230 may be bonded or similarly fixed to the hollow mat 208 and may be an elastomeric material that is hydrophilic or hydrophobic. A hydrogel-material may be included with the flexible membrane 230 for helping the flexible membrane 230 present a smooth surface to the tissue site 101 when activated by fluids. Microperforations (not shown) or valves may be present on the flexible membrane 230 for aiding in the transmission of pressure and fluids. In FIG. 4C, the flexible membrane 230 is continuous and may be deformed by the extendable projections 216 when the pressure ($p_1$) within the inner chamber 211 becomes greater than the pressure ($p_2$) in the recesses 212. The deformation of the flexible membrane 230 by the extendable projections 216 presents a sufficiently rough and uneven surface to the tissue site 101 for promoting granulation. In FIG. 4D, the flexible membrane 230 has slits coinciding with each extendable projection 216 so that when the pressure ($p_1$) within the inner chamber 211 is greater than the pressure ($p_2$) in the recesses 212, the extendable projection 216 deforms the slits on the flexible membrane 230 allowing a portion of the extendable projection 216 to be in direct contact with the tissue site 101. In FIG. 4E, the flexible membrane 230 has flaps'coinciding with each extendable projection 216. The flaps completely covers the plurality of recesses 212 when the pressure ($p_1$) within the inner chamber 211 is less than the pressure ($p_2$) in the recesses 212. When the pressure ($p_1$) within the inner chamber 211 is greater than the pressure ($p_2$) in the recesses 212, the extendable projection 216 deforms the flaps on the flexible membrane 230 allowing a portion of the extendable projection 216 to be in direct contact with the tissue site 101. The use of the flexible membrane 230 may aid the wound healing apparatus 206 in the epithelialisation configuration by helping to present a sufficiently smooth surface to the tissue site. The flexible membrane 230 may be used with any of the disclosed embodiments for the wound healing apparatus 206.

Figure 5A:
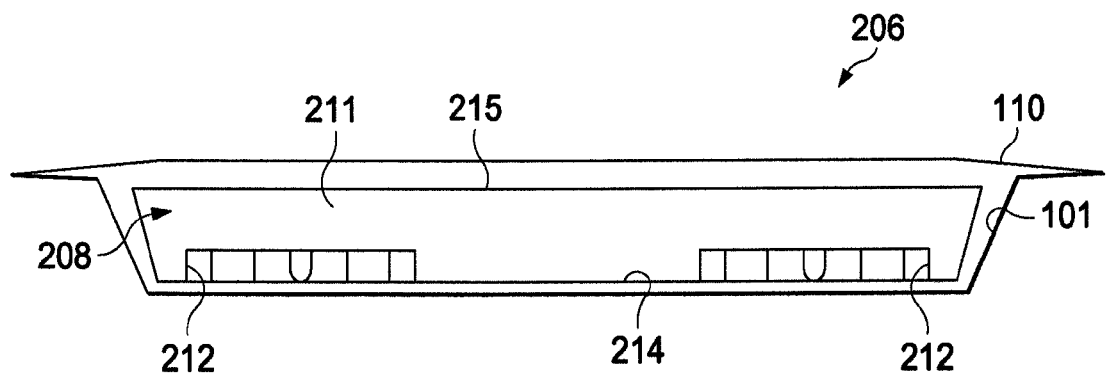
FIG. 5A illustrates a cross-sectional view of another illustrative, non-limiting embodiment of a wound healing apparatus in a state for promoting epithelialisation.
Figure 5B:
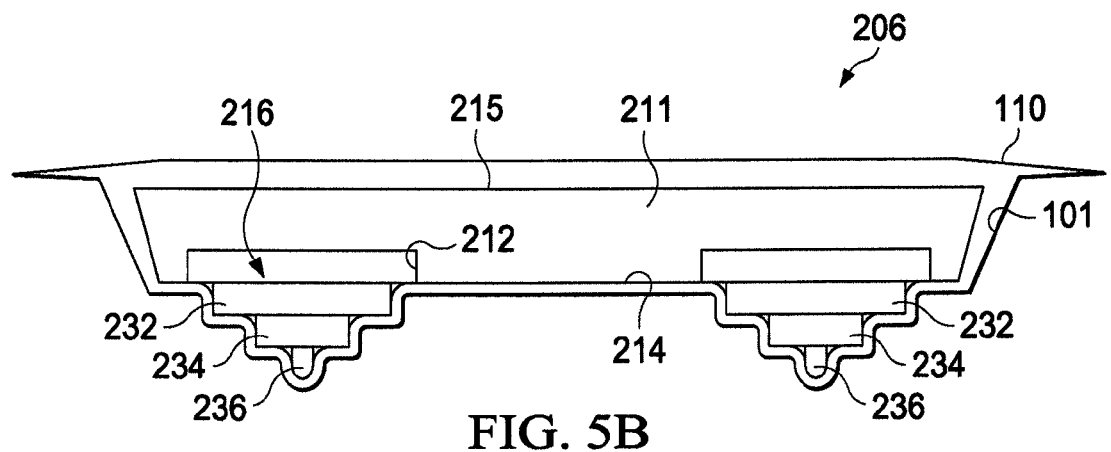
FIG. 5B illustrates a cross-sectional view of the wound healing apparatus of FIG. 5A in a state for promoting granulation.

Referring now to FIGS. 4A-5B and specifically to FIGS. 5A and 5B, another illustrative embodiment of the wound healing apparatus 206 of FIGS. 4A, and 4B is presented. As presented, the wound healing apparatus 206 has a first configuration for promoting epithelialisation shown in FIG. 5A and a second configuration for promoting granulation shown in FIG. 5B. In this embodiment, the extendable projections 216 have a telescoping configuration. The extendable projections 216 include a first section 236, a second section 234, and a third section 232. When the pressure ($p_1$) within the inner chamber 211 is less than the pressure ($p_2$) in the recesses 212, the first section 236, the second section 234, and the third section 232 remain tucked within the recesses 212 presenting a smooth surface to the tissue site 101 for promoting epithelialisation. When the pressure ($p_1$) within the inner chamber 211 is greater than a pressure ($p_2$) in the recesses 212, the extendable projections 216 extend from the recesses 212 in a telescoping configuration for promoting granulation. In the telescoping configuration, the third section 232 extends beyond the first surface 214 of the hollow mat 208, the second section 234 extends beyond the third section 232, and the first section 236 extends beyond the second section 234.

Figure 6A:
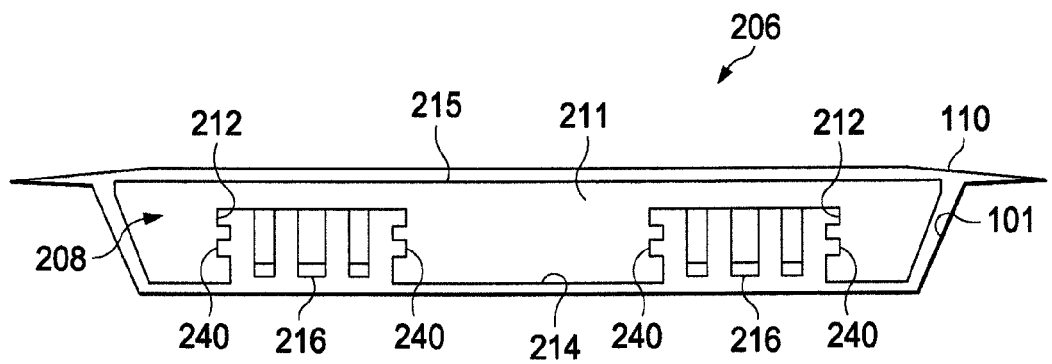
FIG. 6A illustrates a cross-sectional view of another illustrative, non-limiting embodiment of a wound healing apparatus in a state for promoting epithelialisation.
Figure 6B:
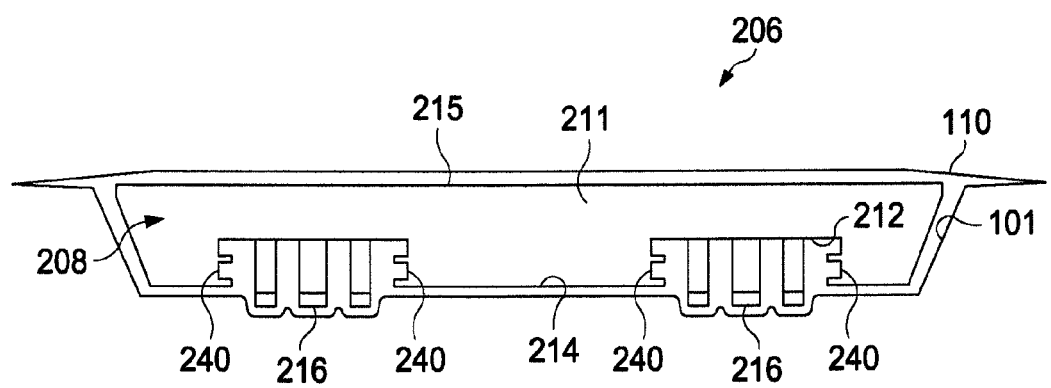
FIG. 6B illustrates a cross-sectional view of the wound healing apparatus of FIG. 6A in a state for promoting granulation.

Referring now to FIGS. 4A, 4B, 6A, and 6B and specifically to FIGS. 6A and 6B, another illustrative embodiment of the wound healing apparatus 206 of FIGS. 4A, and 4B is presented. As shown, the wound healing apparatus 206 has a first configuration for promoting epithelialisation as shown in FIG. 6A and a second configuration for promoting granulation as shown in FIG. 6B. In this embodiment, the plurality of recesses 212 have a bellows configuration. In the bellows configuration, the plurality of recesses 212 have one or more side walls 240 that may be either corrugated, comprised of a plurality of interleaved bends, or comprised of a plurality of furrows. The one or more side walls 240 are configured to collapse when the pressure ($p_1$) within the inner chamber 211 is greater than a pressure ($p_2$) in the recesses 212 so that the extendable projections 216 may extend from the recesses 212 and into the tissue site 101.

Figure 7A:
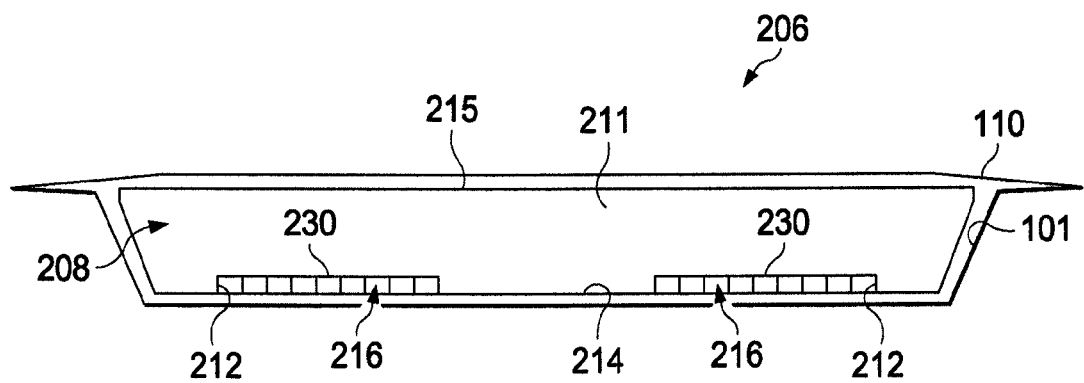
FIG. 7A illustrates a cross-sectional view of another illustrative, non-limiting embodiment of a wound healing apparatus in a state for promoting epithelialisation.
Figure 7B:
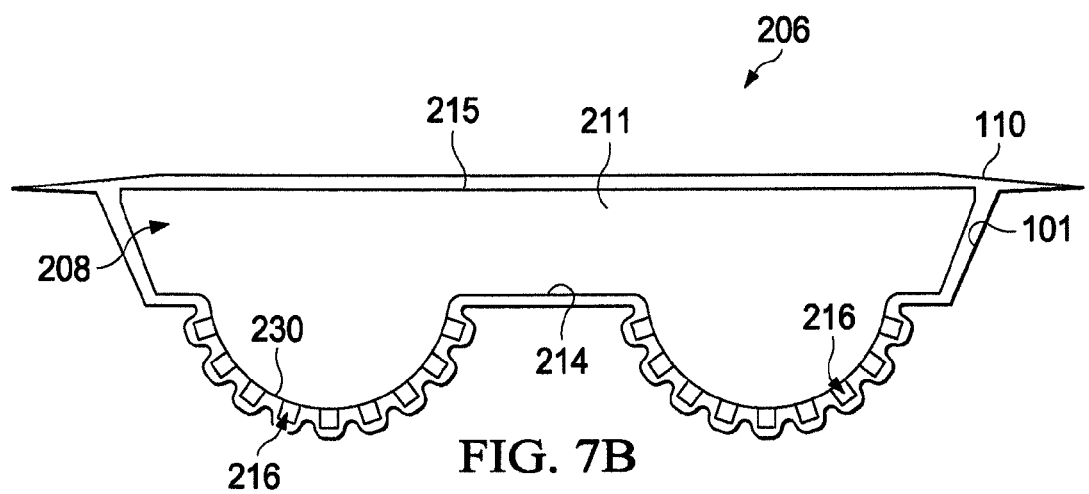
FIG. 7B illustrates a cross-sectional view of the wound healing apparatus of FIG. 7A in a state for promoting granulation.

Referring now to FIGS. 4A, 4B, 7A, and 7B and specifically to FIGS. 7A and 7B, another illustrative embodiment of the wound healing apparatus 206 of FIGS. 4A, and 4B is presented. As shown, the wound healing apparatus 206 has a first configuration for promoting epithelialisation as shown in FIG. 7A and a second configuration for promoting granulation as shown in FIG. 7B. In this embodiment, the extendable projections 216 are connected to the flexible membrane 230 that may be an elastomeric material. When the pressure ($p_1$) within the inner chamber 211 is less than the pressure ($p_2$) in the recesses 212, the extendable projections 216 are tucked inside the recesses 212 and flush with the first surface 214, presenting a smooth surface to the tissue site 101 for promoting epithelialisation. When the pressure ($p_1$) within the inner chamber 211 is greater than a pressure ($p_2$) in the recesses 212, the flexible membrane extends beyond the first surface 214 pushing the extendable projections 216 into the tissue site 101 for promoting granulation.

The various configuration of wound healing apparatus 206 illustrated in FIGS. 4A, 4B, 4C, 4D, 4E, 5A, 5B, 6A, 6B, 7A, and 7B may, in operation, be subjected to reduced pressures similar to those described previously with reference to wound healing apparatus 106. Depending on the configuration of the wound healing apparatus 206, a particular pressure or range of pressures may be used to alter a surface of the wound healing apparatus 206 adjacent the tissue site, thereby encouraging granulation or epithelialisation.

Figure 8A:
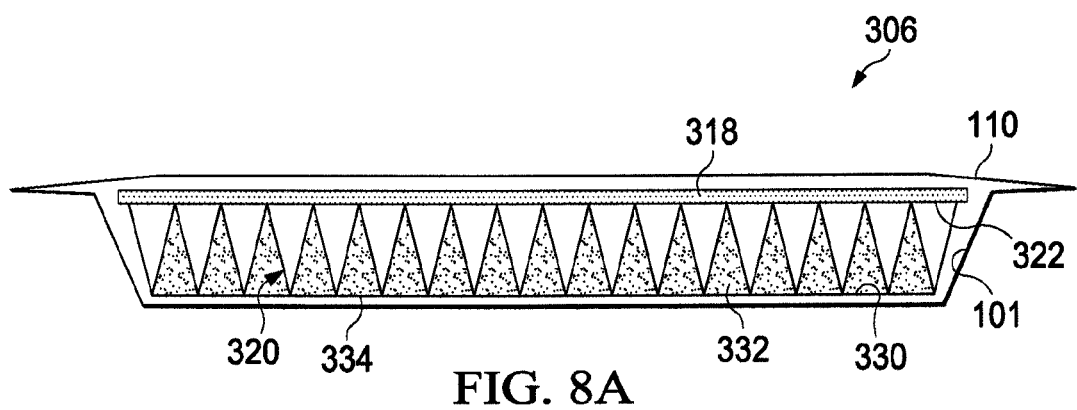
FIG. 8A illustrates a cross-sectional view of another illustrative, non-limiting embodiment of a wound healing apparatus in a state for promoting epithelialisation.
Figure 8B:
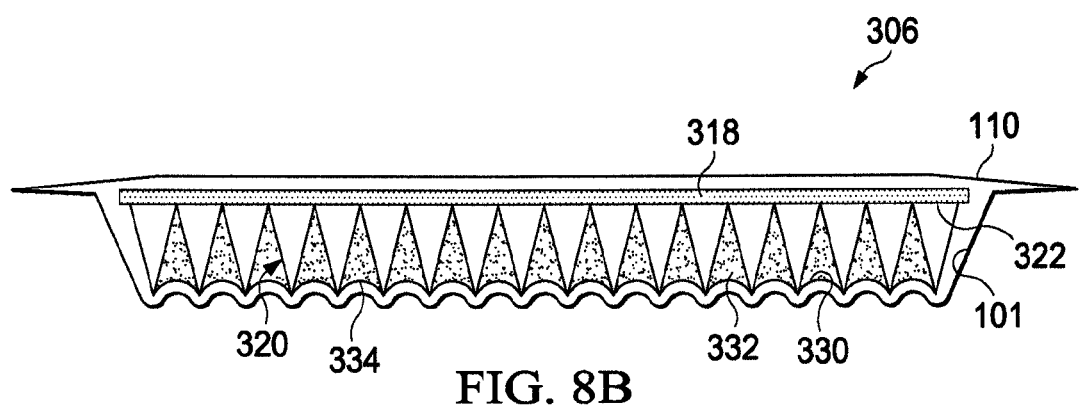
FIG. 8B illustrates a cross-sectional view of the wound healing apparatus of FIG. 8A in a state for promoting granulation.

Referring now to FIGS. 8A and 8B, an illustrative embodiment of a wound healing apparatus 306 positioned proximate the tissue site 101 and covered with the drape 110 is presented. The wound healing apparatus 306 may be used with a reduced pressure treatment system such as the reduced pressure treatment system 100 of FIG. 1. The wound healing apparatus 306 includes a porous pad 332 and a plurality of granulation promoters 320 embedded within the porous pad 332. The wound healing apparatus 306 has a first configuration for promoting epithelialisation as shown in FIG. 8A and a second configuration for promoting granulation as shown in FIG. 8B.

The porous pad 332 may be made of a polyurethane, open-cell, reticulated foam such as GranuFoam® material manufactured by Kinetic Concepts, Incorporated of San Antonio, Tex. The porous pad 332 has a first compressibility ($C_1$) less than, a second compressibility ($C_2$) of the plurality of granulation promoters 320; i.e., the porous pad 332 is softer than, and will compress before, the plurality of granulation promoters 320. The porous pad 332 may help distribute any forces (e.g., body weight) applied to the wound healing apparatus 306 when reduced pressure is not applied to minimize potential high pressure points at the tissue site 101 caused from the plurality of granulation promoters 320.

The plurality of granulation promoters 320 may be any shape or size; for example the plurality of granulation promoters 320 may be spikes, rods, pins, tubes, or other protrusions, etc. The plurality of granulation promoters 320 may be made from a range of, polymers such as a polyurethane (PU), thermoplastic elastomer (TPE), or silicone elastomer material and thus, the second compressibility ($C_2$) may have a range of compressibility or hardness such as $10°$-$100°$ Shore A. In a complementary fashion, the first compressibility ($C_1$) of the porous pad 332 may have a compressibility or hardness of $<10°$-$<100°$ Shore A, depending on the second compressibility ($C_2$) of the plurality of granulation promoters 320 and the degree of granulation desired. Structurally, the plurality of granulation promoters 320 may be solid, perforated, hollow, etc., or any combination thereof. Additionally, the plurality of granulation promoters 320 may be bioabsorbable and may contain a hydrogel-forming material. In one embodiment, the porous pad 332 may contain a hydrogel-forming material to promote epithelialisation as a liquid is introduced to the porous pad. The configuration of the plurality of granulation promoters 320 (the shape and structure) may enable the transmission of pressure and fluid through the plurality of granulation promoters 320 as well as modify the compressibility of the plurality of granulation promoters 320 depending on the material used.

The plurality of granulation promoters 320 may be near a tissue-facing side 334 of the porous pad 332, and in one embodiment, the plurality of granulation promoters 320 may extend from a surface 322 of a substantially gas impermeable, flexible mat 318 in a similar manner as described with reference to the wound healing apparatus 106 of FIGS. 2A and 2B.

The wound healing apparatus 306 may include a flexible membrane 330 positioned adjacent the tissue-facing side 334 of the porous pad 332. The flexible membrane 330 is sufficiently flexible to be deformed by at least a portion of the plurality of granulation promoters 320. The flexible membrane 330 may be an elastomeric material.

The flexible membrane 330 may be deformed by the plurality of granulation promoters 320 when a biasing force, or other activation stimulus, is exerted on the porous pad 332 or the substantially gas impermeable, flexible mat 318 and the biasing force is greater than or equal to a threshold force. When the biasing force is greater than or equal to a threshold force, the plurality of granulation promoters 320 extend from the porous pad 332 or alter the tissue facing side 334 of the porous pad 332. In one embodiment, the flexible membrane 330 may be deformed by the plurality of granulation promoters 320 when the biasing force exerted on the plurality of granulation promoters 320 is greater than or equal to the threshold force. The biasing force may be in the form of reduced pressure supplied from the reduced pressure source 116 of FIG. 1. In a specific, non-limiting embodiment, the threshold force may be a pressure greater than or equal to about −125 mmHg.

The flexible membrane 330 may include microperforations (not shown) or valves that may expand under the influence of the biasing force. In one embodiment, the microperforations expand when the flexible membrane 330 is deformed by the plurality of granulation promoters 320 to allow for the transmission of pressure and fluids. The microperforations may be positioned so as to coincide with each of the granulation promoters 320. A sufficiently smooth surface for encouraging epithelialisation is presented when the microperforations are closed or the flexible membrane 330 is in an unexpanded state. In one embodiment, using the Verein Deutscher Ingenieure (VDI) (3400) standard scale, a sufficiently smooth surface for promoting epithelialisation may have a surface finish of VDI (3400)<30. In a specific, non-limiting embodiment, the microperforations may be closed when the biasing force is at pressures less than about −50 mmHg. Pressures in a range between about −50 mmHg and—about −125 mmHg may be sufficient to cause the microperforations to open and expand without causing the flexible membrane 330 to deform and the porous pad 332 to compress. When the flexible membrane 330 is deformed by the plurality of projections 120 and the porous pad 332 compresses, the microperforations may also expand to allow for the transmission of pressure and fluids. The deformation of the flexible membrane 330 and the compression of the porous pad 332 presents a rough, porous surface to the tissue site 101 for encouraging granulation. In one embodiment, a rough, porous surface may have a surface finish of VDI (3400)>30.

The wound healing apparatus 306 illustrated in FIGS. 8A and 8B may, in operation, be subjected to reduced pressures similar to those described previously with reference to wound healing apparatus 106. Depending on the configuration of the wound healing apparatus 306, a particular pressure or range of pressures may be used to alter a surface of the wound healing apparatus 306 adjacent the tissue site, thereby encouraging granulation or epithelialisation.

Figure 9A:
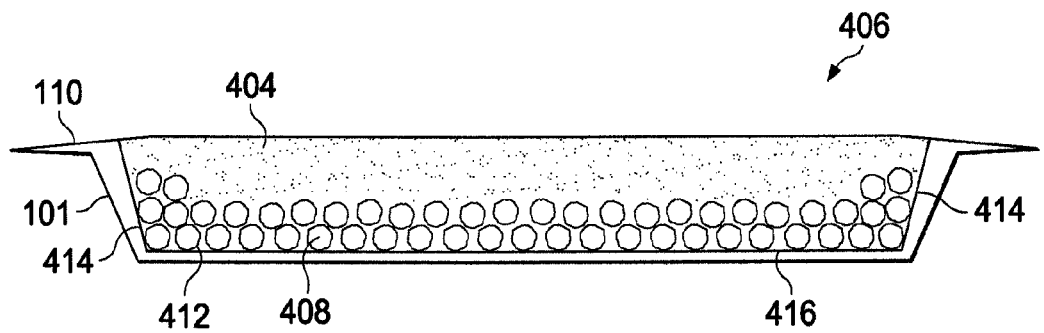
FIG. 9A illustrates a cross-sectional view of another illustrative, non-limiting embodiment of a wound healing apparatus with a hydrogel in an unexpanded state.
Figure 9B:
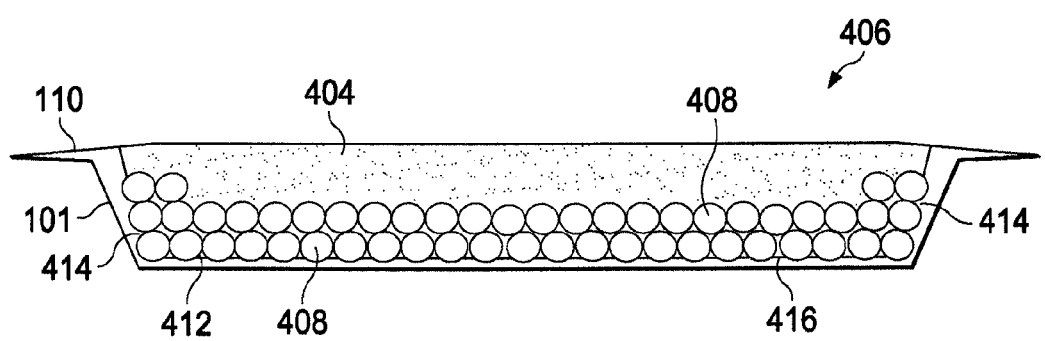
FIG. 9B illustrates a cross-sectional view of the wound healing apparatus of FIG. 9A with the hydrogel in an expanded state.

Referring now to FIGS. 9A and 9B, an illustrative embodiment of a wound healing apparatus 406 positioned proximate the tissue site 101 and covered with the drape 110 is presented. The wound healing apparatus 406 includes a granulation-promoting material having a hydrogel-forming material 408 in a least a portion of the granulation-promoting material. In one embodiment, the granulation-promoting material is a porous, reticulated foam 404. The wound healing apparatus 406 has a first configuration for promoting epithelialisation as shown in FIG. 9B and a second configuration for promoting granulation as shown in FIG. 9A.

The porous, reticulated foam 404 may be an polyurethane, open-cell, reticulated foam such as GranuFoam® material manufactured by Kinetic Concepts, Incorporated of San Antonio, Tex. The porous, reticulated foam 404 has a tissue-contacting surface 412 that is sufficiently rough to promote granulation. When moisture in an amount greater than the moisture content of the gel is presented to the porous, reticulated foam 404, the porous, reticulated foam 404 causes the hydrogel-forming material to moisten and expand, thereby altering the tissue-contacting surface 412 to be sufficiently smooth to promote epithelialisation. The altered tissue-contacting surface 412 presents a moist, smooth surface to the tissue site 101. The tissue-contacting surface 412 may include a base surface 416 and one or more side surfaces 414. In one embodiment, the hydrogel-forming material 408 releases moisture in the presence of a reduced pressure greater than a threshold amount causing the hydrogel-forming material 408 to shrink and the porous, reticulated foam 404 to present a sufficiently rough surface to promote granulation. In another embodiment, the hydrogel-forming material 408 absorbs moisture in the presence of reduced pressure less than the threshold amount causing the hydrogel-forming material to expand and present the tissue-contacting surface 412 that is sufficiently smooth to promote epithelialisation.

In an embodiment where the threshold amount is a pressure of about −25 mm Hg, gauge pressures between about −25 mm Hg and about −125 mm Hg (and extending beyond about −125 mm Hg) may be applied to the space beneath drape 110 to promote granulation tissue growth. At these reduced pressures, a sufficient amount of moisture from the hydrogel-forming material 408 is removed, causing the hydrogel-forming material 408 to contract, thereby exposing the rough surface of the reticulated foam 404 to the tissue site 101. The rough surface promotes granulation by exposing the tissue site 101 to microstrains and microstresses. As the gauge pressure beneath the drape 110 is changed to be between about 0 mm Hg and about −25 mm Hg, moisture is absorbed by the hydrogel-forming material 408, thereby causing the hydrogel-forming material 408 to expand such that a smooth surface is presented to the tissue site 101. The hydrogel-forming material 408 retains the moisture even in the presence of the reduced pressure, which allows continued removal of excess exudate from the tissue site 101.

While a number of discrete embodiments have been described, aspects of each embodiment may not be specific to only that embodiment and it is specifically contemplated that features of embodiments may be combined with features of other embodiments. It also should be apparent from the foregoing that an invention having significant advantages has been provided. While the invention is shown in only a few of its forms, it is susceptible to various changes and modifications without departing from the spirit thereof.

We claim:

1. An apparatus for dressing a wound, comprising:
a substantially gas impermeable, flexible mat;
a plurality of projections extending from a surface of the substantially gas impermeable, flexible mat, each projection having a first end connected to the surface and a second end opposing the first end; and
a flexible membrane positioned adjacent the second end of at least a portion of the plurality of projections, the flexible membrane being deformable by the at least a portion of the plurality of projections when a biasing force exerted on the substantially gas impermeable, flexible mat or the plurality of projections is greater than or equal to a threshold force, wherein the flexible membrane comprises a smooth surface adapted to promote epithelialization if the biasing force is less than the threshold force and a valve associated with at least one of the plurality of projections to present the smooth surface when the biasing force is less than the threshold force.

2. The apparatus of claim 1, wherein the substantially gas impermeable, flexible mat includes a plurality of channels to allow passage of fluids through the substantially gas impermeable, flexible mat.

3. The apparatus of claim 1, wherein the plurality of projections are hollow.

4. The apparatus of claim 1, wherein the plurality of projections are bioabsorbable.

5. The apparatus of claim 1, wherein the flexible membrane is hydrophilic.

6. The apparatus of claim 1, wherein the flexible membrane includes microperforations configured to expand as the flexible membrane is deformed to allow for a transmission of pressure and fluid.

7. The apparatus of claim 1, wherein a deformation of the flexible membrane presents a rough, porous surface.

8. An apparatus for promoting granulation and epithelialisation at a tissue site, the apparatus comprising:
a mat having an inner chamber and a plurality of recesses disposed on a first surface of the mat; and
an extendable projection positioned within each recess and configured to extend from the recess when a pressure ($p_1$) within the inner chamber is greater than a pressure ($p_2$) in the recess;
wherein the inner chamber is sealed to maintain a static fluid volume.

9. The apparatus of claim 8, wherein the extendable projection includes a telescoping configuration.

10. The apparatus of claim 9, wherein the telescoping configuration includes a first section, a second section, and a third section, and wherein the third section extends beyond the first surface of the mat, the second section extends beyond the third section, and the first section extends beyond the second section when the pressure (p1) within the inner chamber is greater than the pressure (p2) in the recess.

11. The apparatus of claim 8, wherein the plurality of recesses includes a bellows configuration.

12. The apparatus of claim 11, wherein the bellows configuration includes at least one sidewall with a plurality of interleaved bends.

13. The apparatus of claim 11, wherein the bellows configuration includes at least one corrugated sidewall.

14. The apparatus of claim 11, wherein the bellows configuration includes at least one sidewall with a plurality of furrows.

15. The apparatus of claim 8 further comprising a flexible membrane positioned to cover at least a portion of the plurality of recesses.

16. The apparatus of claim 15, wherein the flexible membrane includes a plurality of microperforations.

17. The apparatus of claim 8, wherein the apparatus is configured to present a rough surface to the tissue site when the pressure (p1) within the inner chamber is greater than the pressure (p2) in the recess, and wherein the apparatus is configured to present a smooth surface to the tissue site when the pressure (p1) within the inner chamber is less than the pressure (p2) in the recess.

18. The apparatus of claim 8 further comprising a pressurization unit for changing the pressure (p1) within the inner chamber.

19. The apparatus of claim 8, wherein:

the mat is adapted to be positioned at the tissue site and sealed beneath a drape; and application of reduced pressure to a sealed space beneath the drape results in extending the extendable projection from the recess.

20. A wound dressing comprising:

a mat that is substantially gas impermeable and flexible;

a flexible membrane; and a plurality of projections extending from the mat to the flexible membrane;

wherein the flexible membrane comprises a valve associated with at least one of the plurality of projections to present a smooth surface when a biasing force on the plurality of projections is less than a threshold force.

* * * * *